(12) United States Patent
Howard et al.

(10) Patent No.: US 10,974,053 B2
(45) Date of Patent: Apr. 13, 2021

(54) IMPLANTABLE DEVICE PROGRAMMING MANAGEMENT

(71) Applicant: Boston Scientific Neuromodulation Corporation, Valencia, CA (US)

(72) Inventors: Joshua Dale Howard, Winnetka, CA (US); Anne M. Pianca, Santa Monica, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 489 days.

(21) Appl. No.: 15/403,783

(22) Filed: Jan. 11, 2017

(65) Prior Publication Data

US 2017/0197086 A1   Jul. 13, 2017

Related U.S. Application Data

(60) Provisional application No. 62/277,753, filed on Jan. 12, 2016.

(51) Int. Cl.
*A61N 1/372* (2006.01)
*H04W 4/60* (2018.01)
*G16H 40/40* (2018.01)
*A61N 1/36* (2006.01)
*H04W 4/80* (2018.01)
(Continued)

(52) U.S. Cl.
CPC ..... *A61N 1/37247* (2013.01); *A61N 1/36071* (2013.01); *A61N 1/37241* (2013.01); *A61N 1/37264* (2013.01); *A61N 1/37282* (2013.01); *G16H 40/40* (2018.01); *H04W 4/60* (2018.02);
(Continued)

(58) Field of Classification Search
CPC ............ A61N 1/37247; A61N 1/36071; A61N 1/37241; H04W 4/60
See application file for complete search history.

(56) References Cited

U.S. PATENT DOCUMENTS 6,609,032 B1 * 8/2003 Woods ............... A61N 1/36071
607/46
7,181,505 B2   2/2007 Haller et al.
(Continued)

FOREIGN PATENT DOCUMENTS

AU   2017206728 B2   3/2020
CN   108472492 A    8/2018
(Continued)

OTHER PUBLICATIONS

"International Application Serial No. PCT/US2017/012987, International Preliminary Report on Patentability dated Jul. 26, 2018", 6 pgs.
(Continued)

*Primary Examiner* — Joseph M Dietrich
(74) *Attorney, Agent, or Firm* — Schwegman Lundberg & Woessner, P.A.

(57) ABSTRACT

An example of a system may include a processor subsystem; and a memory device comprising instructions, which when executed by the processor subsystem, cause the processor subsystem to: receive at an application executing on a user device, a request to modify the application; transmit the request to an administrative user device for approval; receive a response to the request from the administrative user device; and modify a functionality of the application in response to receiving the response.

14 Claims, 9 Drawing Sheets

(51) Int. Cl.
*H04W 84/04* (2009.01)
*H04W 84/12* (2009.01)

(52) U.S. Cl.
CPC ............ *H04W 4/80* (2018.02); *H04W 84/042* (2013.01); *H04W 84/12* (2013.01)

(56) References Cited

U.S. PATENT DOCUMENTS

| | | | |
|---|---|---|---|
| 8,983,615 B2 | 3/2015 | Tahmasian et al. | |
| 2004/0199217 A1 | 10/2004 | Lee et al. | |
| 2006/0190051 A1* | 8/2006 | Gerber ................ | A61N 1/08 607/41 |
| 2014/0012346 A1* | 1/2014 | Gilkerson .......... | A61N 1/36585 607/20 |
| 2014/0074180 A1* | 3/2014 | Heldman ............ | A61B 5/1101 607/45 |
| 2014/0365654 A1 | 12/2014 | Huerto et al. | |
| 2015/0165205 A1 | 6/2015 | Rockweiler et al. | |

FOREIGN PATENT DOCUMENTS

| | | |
|---|---|---|
| JP | 2005518006 A | 6/2005 |
| JP | 2007505698 A | 3/2007 |
| JP | 2013514155 A | 4/2013 |
| JP | 2014514070 A | 6/2014 |
| JP | 2015510780 A | 4/2015 |
| JP | 2019501730 A | 1/2019 |
| WO | WO-2017123613 A1 | 7/2017 |

OTHER PUBLICATIONS

"International Application Serial No. PCT/US2017/012987, International Search Report dated Apr. 24, 2017", 4 pgs.

"International Application Serial No. PCT/US2017/012987, Written Opinion dated Apr. 24, 2017", 6 pgs.

"Australian Application Serial No. 2017206728, First Examination Report dated Feb. 17, 2019", 3 pgs.

"European Application Serial No. 17701250.7, Response filed Mar. 21, 2019 to Communication Pursuant to Rules 161 and 162 mailed Sep. 18, 2018", 3 pgs.

"Japanese Application Serial No. 2018-536385, Notification of Reasons for Refusal dated Jul. 29, 2019", w/ English translation, 10 pgs.

"Australian Application Serial No. 2017206728, Response filed Nov. 5, 2019 to First Examination Report dated Feb. 17, 2019", 13 pgs.

"Japanese Application Serial No. 2018-536385, Notification of Reasons for Refusal dated Dec. 16, 2019", with English Translation, 11 pgs.

"Japanese Application Serial No. 2018-536385, Response filed Oct. 30, 2019 to Notification of Reasons for Refusal dated Jul. 29, 2019", w/ English Claims, 9 pgs.

\* cited by examiner

_US 10,974,053 B2_

IMPLANTABLE DEVICE PROGRAMMING MANAGEMENT

CLAIM OF PRIORITY

This application claims the benefit of priority under 35 U.S.C. § 119(e) of U.S. Provisional Patent Application Ser. No. 62/277,753, filed on Jan. 12, 2016, which is herein incorporated by reference in its entirety.

TECHNICAL FIELD

This document relates generally to medical devices, and more particularly, to systems, devices, and methods for managing programming of such devices.

BACKGROUND

Neuromodulation, which includes neurostimulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (PG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

The neurostimulation energy may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc.

Recent research has shown that the efficacy and efficiency of certain neurostimulation therapies can be improved, and their side-effects can be reduced, by using patterns of neurostimulation pulses that emulate natural patterns of neural signals observed in the human body.

SUMMARY

Example 1 includes subject matter (such as a device, apparatus, or machine) comprising: a processor subsystem; and a memory device comprising instructions, which when executed by the processor subsystem, cause the processor subsystem to: receive at an application executing on a user device, a request to modify the application; transmit the request to an administrative user device for approval; receive a response to the request from the administrative user device; and modify a functionality of the application in response to receiving the response.

In Example 2, the subject matter of Example 1 may include, wherein the request to modify the application comprises a request to add a new feature to the application.

In Example 3, the subject matter of any one of Examples 1 to 2 may include, wherein the response is provided by a physician using the administrative user device.

In Example 4, the subject matter of any one of Examples 1 to 3 may include, instructions which when executed by the processor subsystem, cause the processor subsystem to connect with an application repository to obtain a different version of the application after receiving the response to the request, and wherein the instructions to modify the functionality of the application comprise instructions to install the different version of the application in place of the application.

In Example 5, the subject matter of any one of Examples 1 to 4 may include, wherein the instructions to modify the functionality of the application in response to receiving the response comprise instructions to enable the new feature in the application.

In Example 6, the subject matter of any one of Examples 1 to 5 may include, wherein the request to modify the application comprises a request to modify stimulation parameters of an implantable pulse generator.

In Example 7, the subject matter of any one of Examples 1 to 6 may include, wherein the instructions to modify the functionality of the application in response to receiving the approval comprise instructions to update the application to program the implantable pulse generator with stimulation parameters.

In Example 8, the subject matter of any one of Examples 1 to 7 may include, wherein the request to modify the application to modify stimulation parameters is made after an evaluation period.

In Example 9, the subject matter of any one of Examples 1 to 8 may include, wherein the evaluation period includes an interaction with a technician to systematically test various stimulation parameters.

In Example 10, the subject matter of any one of Examples 1 to 9 may include, wherein the response to the request is an approval with changes, and wherein the memory includes instructions which when executed by the processor subsystem, cause the processor subsystem to adjust stimulation parameters based on the approval with changes for additional evaluation.

In Example 11, the subject matter of any one of Examples 1 to 10 may include, instructions which when executed by the processor subsystem, cause the processor subsystem to resubmit the request for approval after adjustments to the stimulation parameters.

In Example 12, the subject matter of any one of Examples 1 to 11 may include, wherein the response to the request is a denial of the request, and wherein the memory includes instructions which when executed by the processor subsystem, cause the processor subsystem to present a notification on the user device, the notification a reason why the request was denied.

In Example 13, the subject matter of any one of Examples 1 to 12 may include, wherein the user device comprises a smartphone.

Example 14 includes a machine-readable medium including instructions, which when executed by a machine, cause the machine to perform operations of any of the claims 1-13.

Example 15 includes a method to perform operations of any of the claims 1-13.

Example 16 includes subject matter (such as a device, apparatus, or machine) comprising: a processor subsystem; and a memory device comprising instructions, which when executed by the processor subsystem, cause the processor subsystem to: receive at an application executing on a user device, a request to modify the application; transmit the request to an administrative user device for approval; receive a response to the request from the administrative user device; and modify a functionality of the application in response to receiving the response.

In Example 17, the subject matter of Example 16 may include, wherein the request to modify the application comprises a request to add a new feature to the application.

In Example 18, the subject matter of any one of Examples 16 to 17 may include, wherein the response is provided by a physician using the administrative user device.

In Example 19, the subject matter of any one of Examples 16 to 18 may include, instructions which when executed by the processor subsystem, cause the processor subsystem to connect with an application repository to connect with an application repository to obtain a different version of the application after receiving the response to the request; and wherein the instructions to modify the functionality of the application comprise instructions to install the different version of the application in place of the application.

In Example 20, the subject matter of any one of Examples 16 to 19 may include, wherein the instructions to modify the functionality of the application in response to receiving the response comprise instructions to enable the new feature in the application.

In Example 21, the subject matter of any one of Examples 16 to 20 may include, wherein the request to modify the application comprises a request to modify stimulation parameters of an implantable pulse generator.

In Example 22, the subject matter of any one of Examples 16 to 21 may include, wherein the instructions to modify the functionality of the application in response to receiving the approval comprise instructions to update the application to program the implantable pulse generator with stimulation parameters.

In Example 23, the subject matter of any one of Examples 16 to 22 may include, wherein the request to modify the application to modify stimulation parameters is made after an evaluation period.

In Example 24, the subject matter of any one of Examples 16 to 23 may include, wherein the evaluation period includes an interaction with a technician to systematically test various stimulation parameters.

In Example 25, the subject matter of any one of Examples 16 to 24 may include, wherein the response to the request is an approval with changes, and wherein the memory includes instructions which when executed by the processor subsystem, cause the processor subsystem to adjust stimulation parameters based on the approval with changes for additional evaluation.

In Example 26, the subject matter of any one of Examples 16 to 25 may include, instructions which when executed by the processor subsystem, cause the processor subsystem to resubmit the request for approval after adjustments to the stimulation parameters.

In Example 27, the subject matter of any one of Examples 16 to 26 may include, wherein the response to the request is a denial of the request, and wherein the memory includes instructions which when executed by the processor subsystem, cause the processor subsystem to present a notification on the user device, the notification a reason why the request was denied.

Example 28 includes subject matter (such as a method, means for performing acts, machine readable medium including instructions that when performed by a machine cause the machine to performs acts, or an apparatus to perform) comprising: receiving at an application executing on a user device, a request to modify the application; transmitting the request to an administrative user device for approval; receiving a response of the request from the administrative user device; and modifying a functionality of the application in response to receiving the response.

In Example 29, the subject matter of Example 28 may include, wherein the request to modify the application comprises a request to add a new feature to the application.

In Example 30, the subject matter of any one of Examples 28 to 29 may include, wherein the response is provided by a physician using the administrative user device.

In Example 31, the subject matter of any one of Examples 28 to 30 may include, connecting with an application repository to obtain a different version of the application after receiving the response to the request; and wherein modifying the functionality of the application comprises: installing the different version of the application in place of the application.

In Example 32, the subject matter of any one of Examples 28 to 31 may include, wherein modifying the functionality of the application in response to receiving the response comprises enabling the new feature in the application.

In Example 33, the subject matter of any one of Examples 28 to 32 may include, wherein the request to modify the application comprises a request to modify stimulation parameters of an implantable pulse generator.

In Example 34, the subject matter of any one of Examples 28 to 33 may include, wherein modifying the functionality of the application in response to receiving the approval comprises updating the application to program the implantable pulse generator with stimulation parameters.

Example 35 includes subject matter (such as a machine-readable medium, computer-readable medium, or other stored instructions) comprising instructions, which when executed, cause a device to: receive at an application executing on a user device, a request to modify the application; transmit the request to an administrative user device for approval; receive a response of the request from the administrative user device; and modify a functionality of the application in response to receiving the response.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
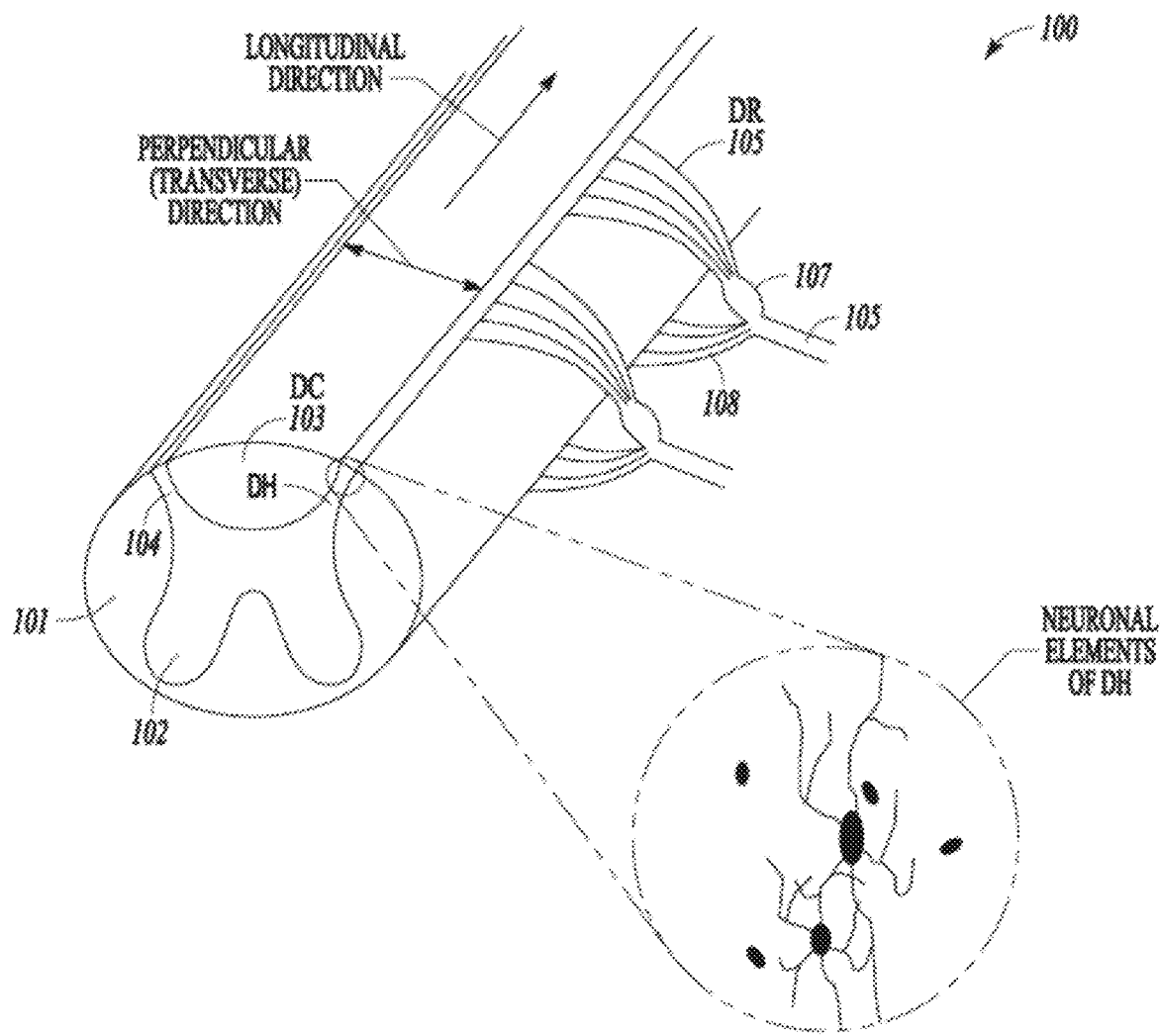
FIG. 1 illustrates a portion of a spinal cord.

Various embodiments described herein involve spinal cord modulation. A brief description of the physiology of the spinal cord and related apparatus is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that am in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies standard SCS therapy. Some embodiments deliver therapy where the delivery of energy is perceptible due to sensations such as paresthesia. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). Sub-perception therapy may include higher frequency modulation (e.g. about 1500 Hz or above) of the spinal cord that effectively blocks the transmission of pain signals in the afferent fibers in the DC. Some embodiments herein selectively modulate DH tissue or DR tissue over DC tissue to provide sub-perception therapy. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100

Hz, By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 70%±5%, 30%±5%, 40%±5%, 50%±5% or 60%±5%. For example, a burst of pulses for 10 ms during a Stimulation ON portion followed by 15 ms without pulses corresponds to a 40% duty cycle.

Figure 2:
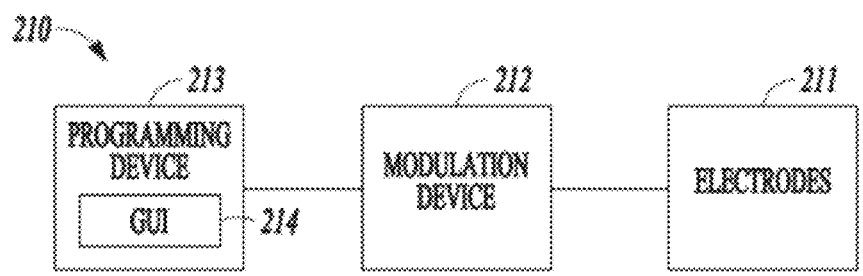
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters, such as modulation parameters specifying the electrical pulses and a selection of electrodes through which each of the electrical pulses is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
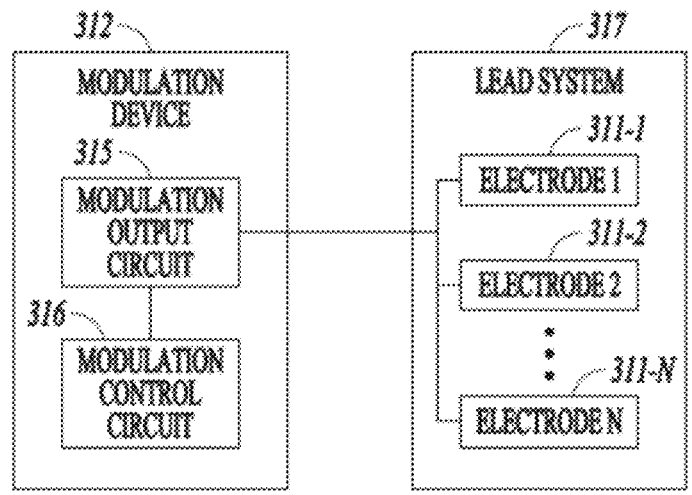
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers neuromodulation pulses. The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of available modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets. A closed-loop mechanism may be used to identify and test modulation parameter sets, receive patient or clinician feedback, and further revise the modulation parameter sets to attempt to optimize stimulation paradigms for pain relief. The patient or clinician feedback may be objective and/or subjective metrics reflecting pain, paresthesia coverage, or other aspects of patient satisfaction with the stimulation.

Figure 4:
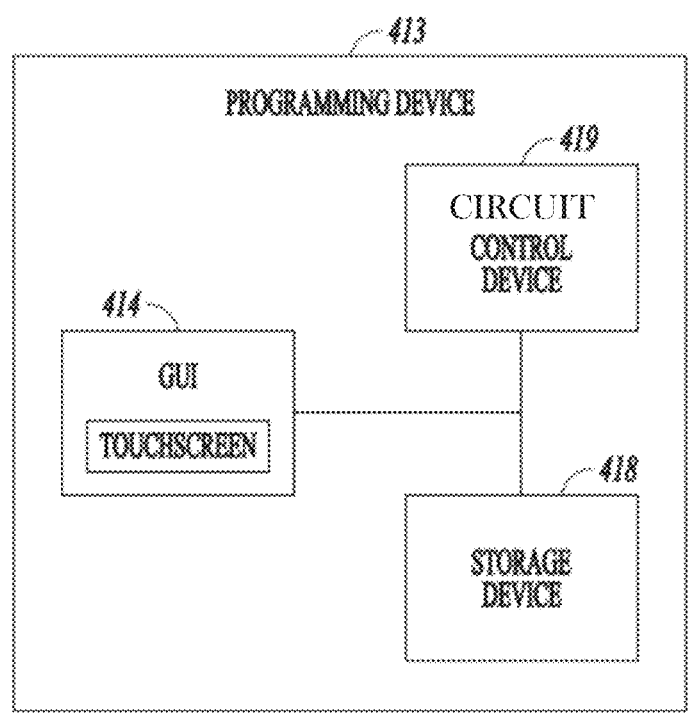
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device (e.g., modulation device 312 of FIG. 3). The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software, and firmware. For example, the circuit of GUI414, modulation control circuit 316, and programming control circuit 419, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or a portion thereof, and a programmable logic circuit or a portion thereof.

Figure 5:
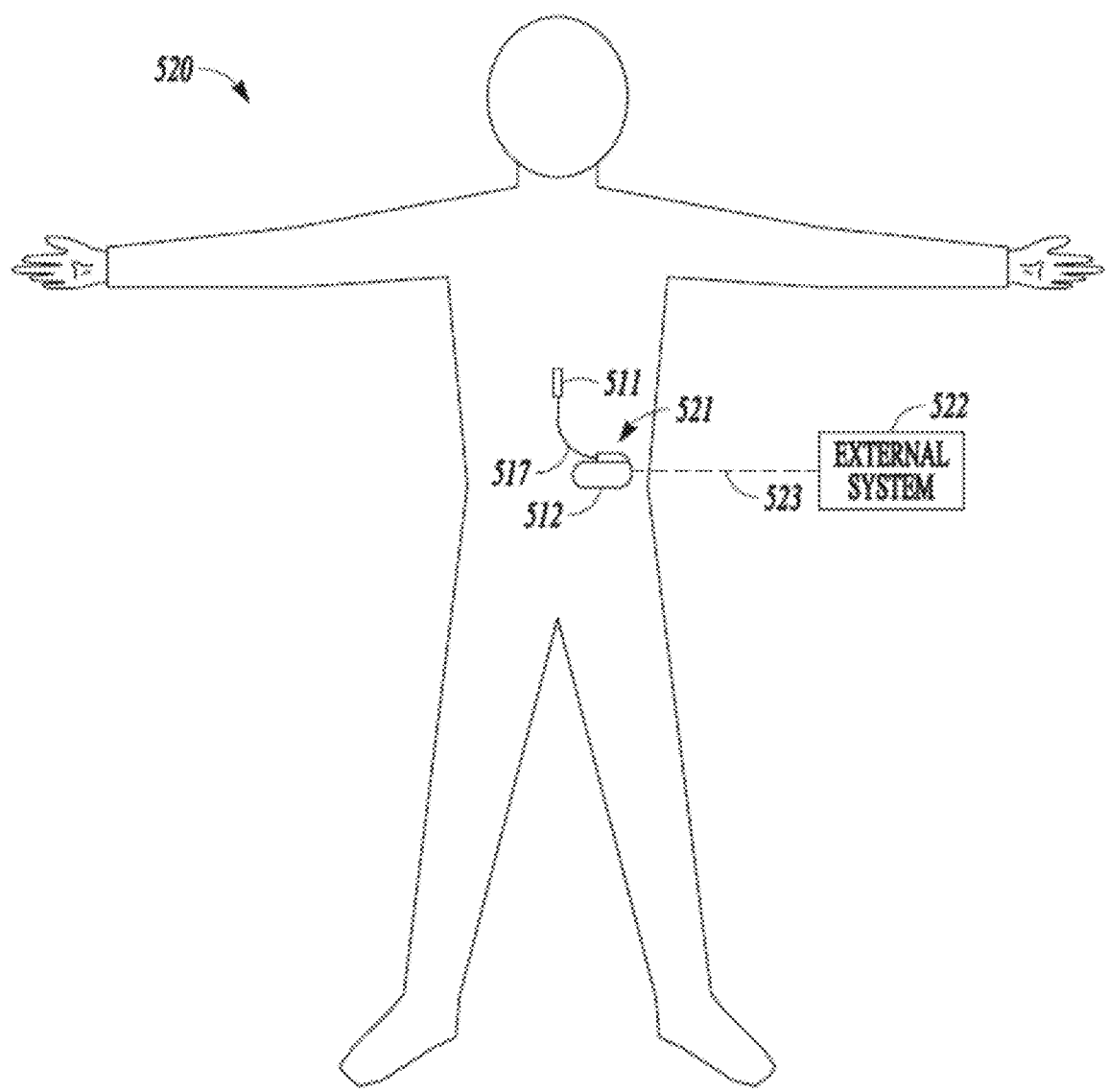
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets. The system 520 includes an implantable system 521, an external system 522, and a telemetry link 523 providing for wireless communication between implantable system 521 and external system 522. The implantable system 521 is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters. The remote control device may also provide a mechanism for the patient to provide feedback on the operation of the implantable neuromodulation system. Feedback may be metrics reflecting perceived pain, effectiveness of therapies, or other aspects of patient comfort or condition.

The neuromodulation lead(s) of the lead system 517 may be placed adjacent, e.g., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
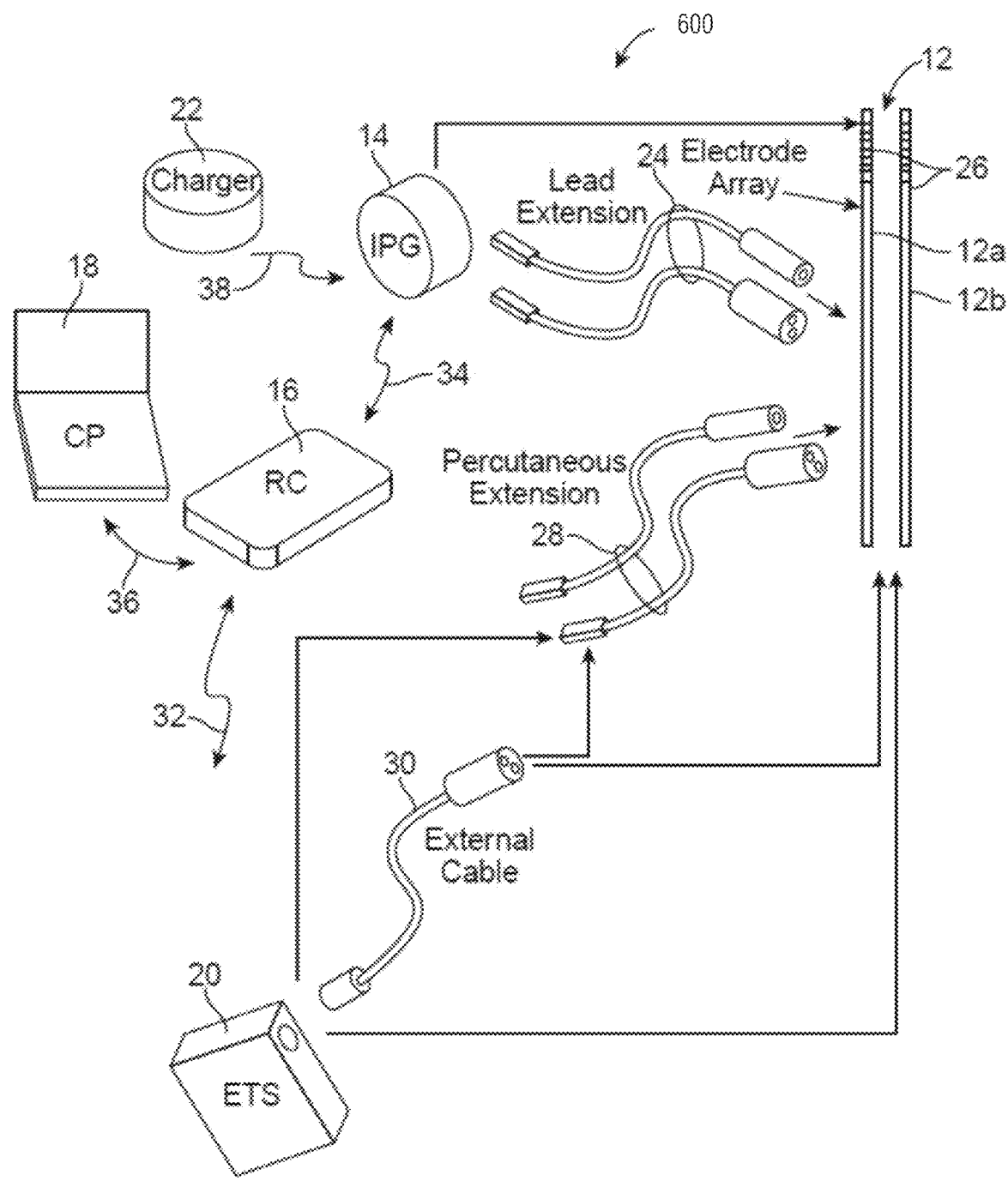
FIG. 6 illustrates, by way of example, an embodiment of an SCS system.

FIG. 6 illustrates, by way of example, an embodiment of an SCS system 600. The SCS system 600 generally comprises a plurality of neurostimulation leads 12 (in this case, two percutaneous leads 12a and 12b), an implantable pulse generator (IPG) 14, an external remote control (RC) 16, a Clinician's Programmer (CP) 18, an External Trial Stimulator (ETS) 20, and an external charger 22.

The IPG 14 is physically connected via two lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead can be used in place of one or more of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and neurostimulation leads 12 can be provided as an implantable neurostimulation kit, along with, e.g., a hollow needle, a stylet, a tunneling tool, and a tunneling straw.

The ETS 20 may also be physically connected via percutaneous lead extensions 28 or external cable 30 to the neurostimulation lead 12. The ETS 20, which has similar pulse generation circuitry as the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the neurostimulation lead 12 has been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides the user detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. For purposes of brevity, the details of the RC 16, ETS 20, and external charger 22 will not be described herein.

Managing Programming Services on a Programmer

For many patients, neurostimulation therapy is an effective option to manage chronic pain. Chronic pain is rarely a static state. Instead, pain typically migrates and mutates affecting different portions of a patient's body and at varying degrees. As such, as a patient's pain changes, so too does the neurostimulation programming that is the most effective at blocking or masking the pain. Generally, a patient's stimulation programming is performed by a clinician or a technician. As patients become more familiar with technology and as technology advances, the patient may be in a better position to modulate stimulation programming according to their perceived pain.

The present disclosure describes several workflows, systems, methods, and devices to provide patients, physicians, insurance companies, and medical device manufacturers improvements to help manage pain better and provide better patient support. For example, patients are provided tools that allow them to manage their own pain better and reduce office visits, thereby reducing their out-of-pocket costs. Physicians are able to review, approve, and correspond with their patients remotely, thereby increasing their patients-per-day throughput, manage patient care better, and increase revenue. Insurance companies are provided a way to easily integrate new patient care modalities into existing systems. Medical device manufacturers and representatives are able to provide additional products and services to patients to help in product support and pain management.

Figure 7:
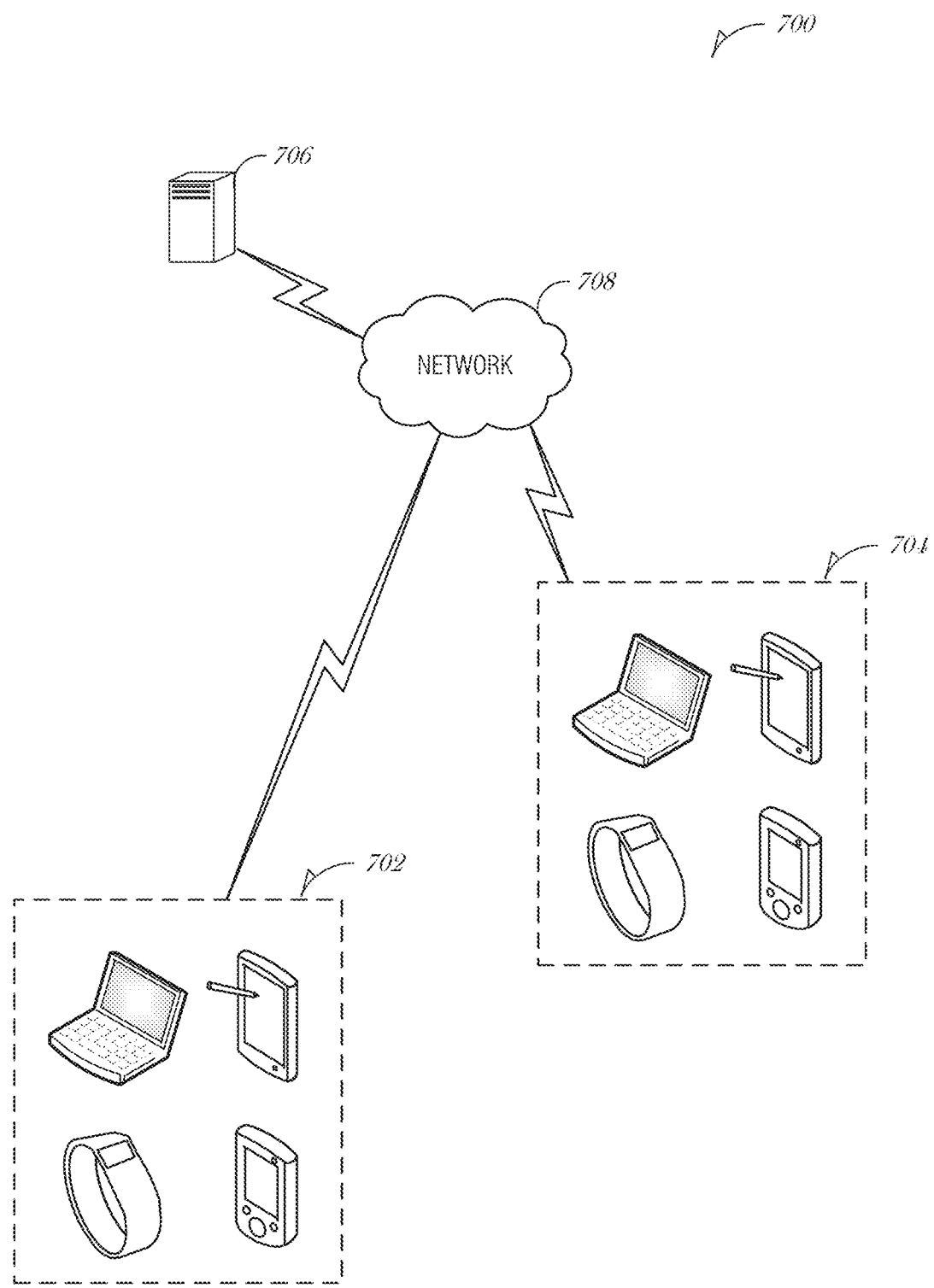
FIG. 7 illustrates, by way of example, an embodiment of data and control flow in a system that utilizes machine learning to optimize neurostimulation patterns.

FIG. 7 illustrates, by way of example, an embodiment of an operational environment 700. The environment 700 includes a user device 702, an administrative device 704, and a server 706, all connected over a network 708. The user device 702 and administrative device 704 may be any type of computing device including, but not limited to a tablet, a desktop computer, a hybrid computer, a laptop, a wearable device (e.g., smartglasses or a smartwatch), a smartphone, a personal digital assistant (PDA), a handheld personal computer, or the like. The server 706 may be one or more computers acting in concert (e.g., in a server farm or a cloud environment) that provide a virtualized server environment. The server 706 may be a conventional server system that provides a service that listens on one or more active ports and processes requests received at such ports. The server 706 may act in response to specific apps on the user device 702 or administrative device 704. The communication to the server 706 from the user device 702 or administrative device 704 may be encrypted or otherwise secured using one or more security mechanisms, such as a public key infrastructure (PKI) scheme (e.g., Diffie-Hellman key exchange, RSA algorithms, etc.) or a symmetric key exchange (e.g., Data Encryption Standard (DES), Advanced Encryption Standard (AES), etc.).

The network 708 may include local-area networks (LAN), wide-area networks (WAN), wireless networks (e.g., 802.11 or cellular network), the Public Switched Telephone Network (PSTN) network, ad hoc networks, personal area networks (e.g., Bluetooth) or other combinations or permutations of network protocols and network types. The network 708 may include a single local area network (LAN) or wide-area network (WAN), or combinations of LAN's or WAN's, such as the Internet. The various devices coupled to the network 708 may be coupled to the network 708 via one or more wired or wireless connections.

Applications (or apps) have become a mainstream commodity. Apps are provided to various computing platforms including tablets, desktops, smartphones, and the like. Apps may be provided to certain operating systems, such as Apple® or Android™, or may be generally available for all popular operating systems. An application may be made available to a user from an online repository (e.g., application store). The online repository may provide applications that have been reviewed and screened by the repository.

The patient may install an app on the user device 702 in order to control the IPG or correspond with a person at the administrative device 704. The administrative device 704 may be used by several different types of people including, but not limited to a physician, a clinician, a specialist, a sales representative, an insurance representative, a customer support representative, or the like.

In operation, the patient may use the user device 702 to program, query, or maintain an IPG. In this manner, the user device 702 acts as a CP, ETS, or RC in various embodiments. The user device 702 may display stimulation parameters, programs, event history, and other aspects of programming or controlling the IPG. The patient may determine that the a particular programming routine is not effective at suppressing or masking pain, and may decide to evaluate a new program. The patient may enter a request to obtain a new program via the user device 702. The request is transmitted to the administrative device 704 via the network 708.

Upon receiving a request, the physician (or similar personnel) may review the patient's file and approve the request. The approval may be sent via the network 708 from the administrative device 704 to the user device 702. The approval may include additional instructions for the patient, which may be displayed on the user device 702. After approval, the new program may be instituted in the IPG using a wireless connection from the user device 702 to the IPG. Alternatively, the user device 702 may be used to direct a CP, ETC, or RC to interact with the IPG in order to program the IPG.

Because of the number of electrodes available combined with the ability to generate a variety of complex electrical pulses, a huge selection of available modulation parameter sets may be available to the clinician or patient for programming. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets. A closed-loop mechanism may be used to identify and test modulation parameter sets, receive patient or clinician feedback, and further revise the modulation parameter sets to attempt to optimize stimulation paradigms for pain relief. The patient or clinician feedback may be objective and/or subjective metrics reflecting pain, paresthesia coverage, or other aspects of patient satisfaction with the stimulation. Thus, this cycle may be used more than once by the patient to request changes to programming from the physician by way of the user device 702 to administrative device 704 pathway.

Software or hardware in the implantable pulse generator (IPG), programming device, or patient remote control may be used during a trial period or after permanent implant to identify the optimal modality. The stimulation patterns may be modulated in both the time and space domains. The stimulation patterns may also be modulated in the informational domain, which refers to the patterns of pulses. The learning system may automatically cycle through different sub-perception modalities (e.g., high frequency, burst, low-mid frequency/low amplitude, etc.), collect patient feedback through a remote control or other system on each of the modalities, and correlate patient feedback with therapy efficacy in order to determine an optimal or improved therapy. This allows for improved or optimal sub-perception therapy to be determined without interaction with the health care provider or manufacturer representative.

An initial set of stimulation patterns may be generated from a domain of all available stimulation patterns. The initial set may be obtained using one or more machine learning or optimization algorithms to search for and identify effective patterns. Alternatively, the initial set may be provided by a clinician.

In addition to the initial set of parameter settings, one or more ranges for one or more parameters may be determined by the system or provided by a user (e.g., clinician). The ranges may be for various aspects including amplitude, pulse width, frequency, pulse pattern (e.g., predetermined or parameterized), cycle on/off properties, spatial location of field, spatial extent of field, and the like.

Estimated times for wash-in and wash-out may be provided by a user or determined by the system. In an embodiment, the system estimates the wash-in/out to be used from the patient feedback. Accurate estimates for wash-in/out are important because over-estimates (e.g., too long of a period) may result in patients having unnecessary pain because the programming cycles too slowly, and under-estimates (e.g., too short of a period) may result in missing important information because the wash-in has not occurred. So, in an embodiment, a user is able to set the expected wash-in/out times for the learning machine algorithm to use. Alternatively, the IPG programming may begin with the user estimate and then adjust based on data collected from the user or other sources to revise the estimated wash-in or wash-out times.

In the clinical system, a patient may be provided one or more stimulation patterns, which may be tested by the patient with or without clinician supervision. Objective pain metrics, subjective pain metrics, or both objective and subjective pain metrics may be received from the patient, which are used in the machine learning or optimization algorithms to develop further sets of patterns. Objective pain metrics include those that are physiologically expressed, such as EEG activity, heart rate, heart rate variability, galvanic skin response, or the like. Subjective pain metrics may be provided by the patient and be expressed as "strong pain," "lower pain," or numerically in a range, for example. The pain metrics may be communicated using various communication mechanisms, such as wireless networks, tethered communication, short-range telemetry, or combinations of such mechanisms. The patient may manually input some information (e.g., subjective pain scores).

A non-exhaustive list of pain metrics is provided herein. One example of a pain metric is EEG activity (e.g., Theta activity in the somatosensory cortex and alpha and gamma activity in the prefrontal cortex have been shown to correlate with pain). Another example pain metric is fMRI (activity in the anterior cingulate cortex and insula have been shown to correlate with changes in chronic pain). Another example pain metric is fMRI (activity in the pain matrix, which consists of the thalamus, primary somatosensory cortex, anterior cingulate cortex, prefrontal cortex, and cerebellum and is activated in pain conditions). Another example pain metric is heart rate variability, galvanic skin response, cortisol level, and other measures of autonomic system functioning (autonomic system health has been shown to correlate with pain). Another example pain metric is physical activity (amount of physical activity has been shown to correlate with pain). Another example pain metric is pain scores (may be inputted through an interface where the patient selects a point on a visual analog scale, or clicks a number on a numerical rating scale). Another example pain metric is quantitative sensory testing [e.g., spatial discrimination (two-point, location, diameter), temporal discrimination, detection threshold (mechanical, thermal, electrical), pain threshold (mechanical, thermal, electrical), temporal summation, thermal grill] (QST measures have been shown to correlate with pain). Another example pain metric is somatosensory evoked potentials, contact heat evoked potentials (these have been shown to be correlated with pain). Another example pain metric is H-reflex, nociceptive flexion reflex (these have been shown to be reduced by SCS). Another example pain metric is conditioned place preference (e.g., in one chamber, stimulate with one paradigm 1, in other chamber, stimulate with paradigm 2. The chamber where the animal spends the most time wins and continues to the next round). Another example pain metric is local field potential recordings in the pain matrix (recordings of neural activity in these areas are possible with invasive electrodes in a preclinical model).

Some pain metrics are primarily preclinical in nature (e.g., conditioned place preference and local field potential recordings), while others are primarily clinical in nature (e.g., pain scores and quantitative sensory testing). However, it is understood that the pain metrics may be obtained in either preclinical or clinical settings.

Pain metrics may be continuously or repeatedly collected from patients and fed into the machine learning or optimization algorithms to refine or alter the stimulation patterns. For example, the patients may interact with a programmer, remote control, bedside monitor, or other patient device to record physical condition, pain, medication dosages, etc. The patient device may be wired or wirelessly connected to the system with the machine learning system. This closed-loop mechanism provides an advantage of reducing the search domain during repeated iterations of the machine learning or optimization algorithm. By reducing the search domain, a clinician is able to more quickly identify efficacious patterns and a patient may be subjected to shorter programming sessions, which produce less discomfort.

In addition to pain metrics, additional patient feedback may be obtained, such as a satisfaction evaluation, self-reported activity, visual analog scale (VAS), or numerical rating scale (NRS). Other feedback and input may be obtained, such as from a user (e.g., clinician) or sensor values.

The physical system may take on many different forms. Data collected from the patient may be measured using wearable sensors (e.g., heart rate monitor, accelerometer, EEG headset, pulse oximeter, GPS/location tracker, etc.). The pain metrics and other feedback involving manual input may be entered via remote control or other external device used by the patient (e.g. via user device 702).

Figure 8:
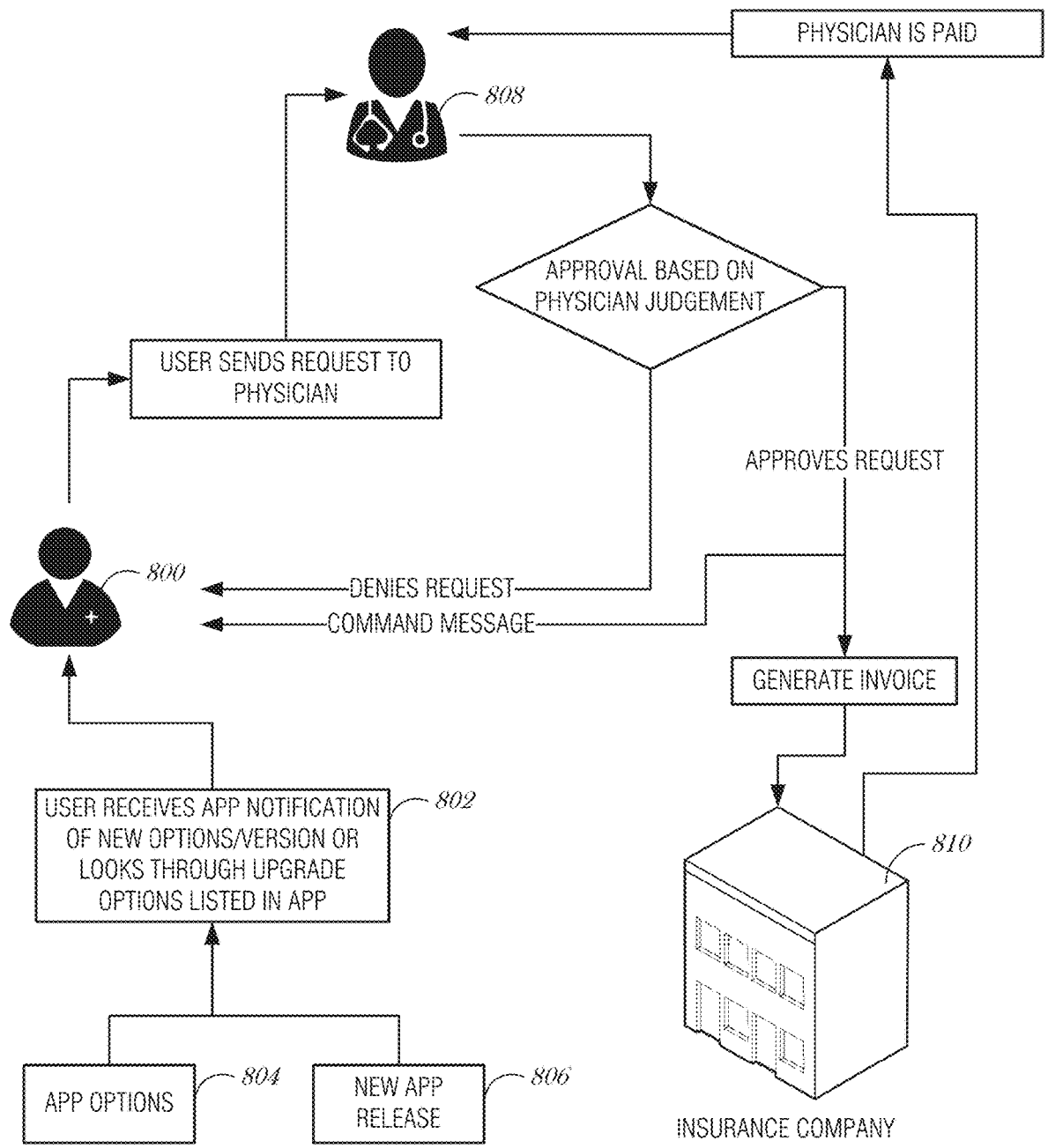
FIG. 8 illustrates, by way of example, an embodiment of data and control flow in a system.

FIG. 8 illustrates, by way of example, an embodiment of data and control flow in a system. A user 800 (e.g., patient) may install an app on a user device. The app may be installed with standard or baseline options and features. While using the app, the user 800 is notified of additional features or a new version of the app (operation 802). For example, after a trial period, the user 800 is provided an opportunity to unlock additional features not initially exposed to the user

800. Such features may be advanced features intended for users with more experience with the app. As another example, the user 800 may be presented an opportunity to add additional features based on a pay-per-feature model. The user 800 may pay for the feature using an in-app purchase model where the user indicates that they want to install or unlock the new feature and the app may prompt the user for confirmation, after which the app may use an underlying payment system to process the in-app purchase. The payment system may have a credit card or other form of payment on record from the user 800, which is then debited the amount of the in-app purchase. The payment may be a copay or coinsurance to cover a patient portion of a cost.

As a specific example, the user 800 may be provided an app that has basic functionality of program selection, activating or deactivating stimulation, and amplitude controls. Additional features may be made available to the user 800, such as the ability to store several programs, the ability to automatically rotate through programs, more fine-tuned control over a program, and the like. Such additional features may be built into the initial installation of the app (option 804) or be provided as ongoing upgrades or improvement from the app creator (option 806).

When a user 800 decides to upgrade or unlock an app's features, the 800 may send a request to a physician 808. The physician 808 may decide to allow the user 800 access to the additional features based on various factors, such as the user's mental condition or capacity, the user's emotional state, the user's physical condition, or the like. The physician 808 may approve or deny the user's request. Should the physician 808 deny the request, then at operation 810, the user 800 may be notified of the denial with optional notes from the physician 808 indicating a reason for denying the request.

Should the physician 808 approve the request for new features or a new version of the app, a control message is transmitted back to the user's device to unlock or install the new feature. The payment for a copay or coinsurance payment, if any, may be processed at this time. In addition, upon approval by the physician 808 an invoice is generated and transmitted to an insurance company 810 (operation 812). The insurance company 810 may then perform the conventional settlement processes, such as by paying the physician's office or the physician 808, paying the app developer or app owner 814, providing an explanation of benefits statement to the user 800, and the like.

Under the workflow illustrated in FIG. 8, insurance costs are reduced because an in-person patient visit is not needed, the physician is compensated for their time with the opportunity for more revenue based on shorter interactions, and the app developer/owner is compensated based on the usage by the user base.

Figure 9:
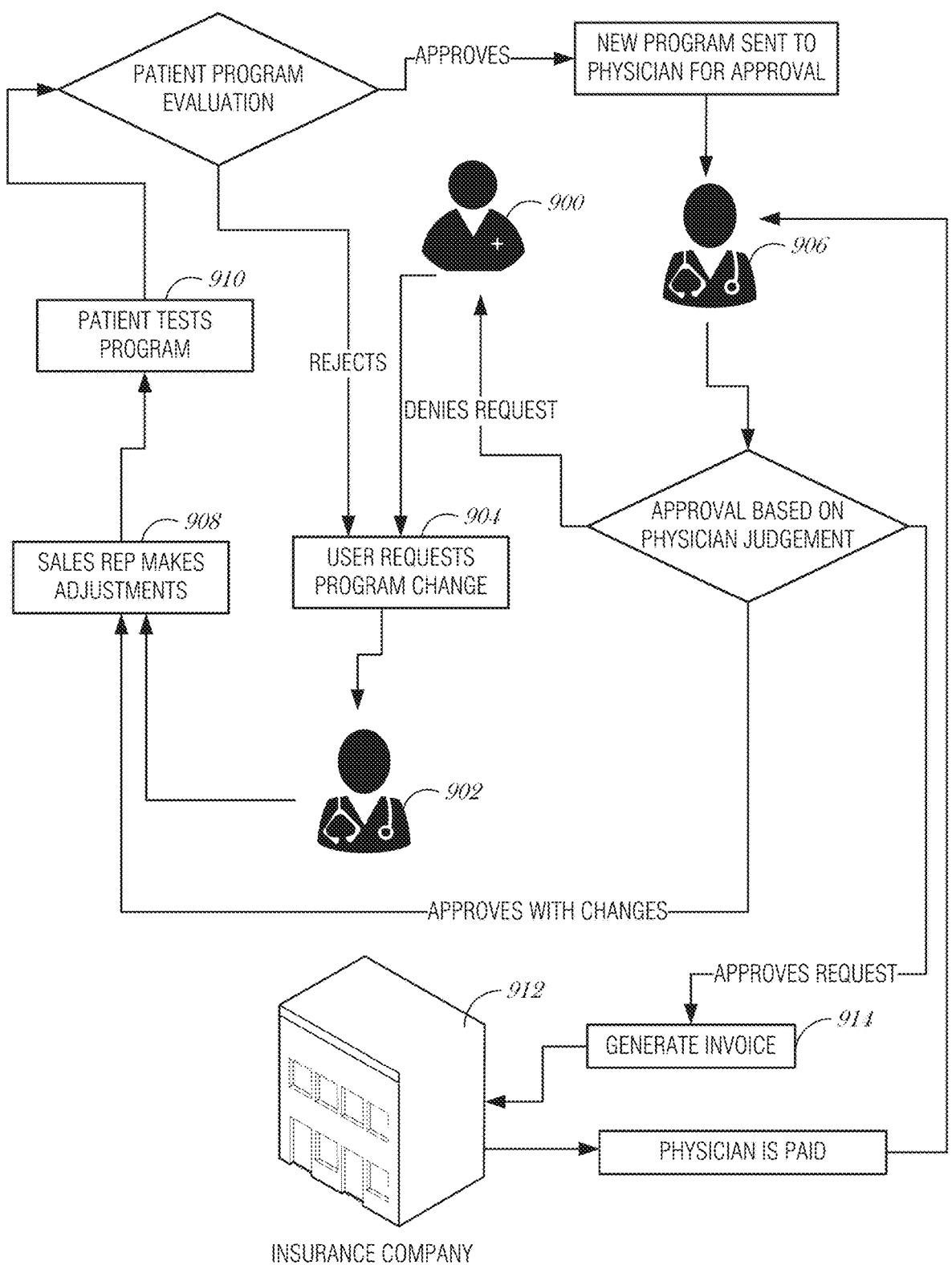
FIG. 9 illustrates, by way of example, another embodiment of data and control flow in a system.

FIG. 9 illustrates, by way of example, another embodiment of data and control flow in a system. A user 900 is fitted with an implanted medical device (IMD). The implantable medical device maybe an implantable neurostimulation system, in an example, and may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy. The user 900 may use a user device (e.g., user device 702) as the external programming device.

As the user 900 experiences changes in their daily pain, they may decide to change the programming of their IMD. The user 900 requests a change to a sales representative 902 (operation 904). The sales representative 902 may act as a technical liaison to a physician 906 and assist the user 900 in selecting an effective programming for the user 900. As such, the sales representative 902 may make adjustments to the programming (operation 908) and the user 900 (e.g., patient) may test the program for a short period of time, e.g., 5 minutes. User interface controls may be provided to a person (e.g., user 900, sales representative 902, or physician 906) to set test periods for a program, manage wash-in/out time, provide user reports with raw data or compiled data (e.g., charts, graphs, summaries), or control alternating programs. For example, a "best so far" (BSF) program may be used and reused over time to ensure that the patient experiences a good percentage of effective stimulation. The BSF program may be used as every other program, every third program, or in other ways to allow the system to test additional programs in between the BSF program.

The user 900 may evaluate the reprogramming (operation 910). Should the user 900 reject the reprogramming, then the user 900 may interact with the sales representative 902 to request another program change (operation 904) and iterate through testing a subsequent reprogramming. When the user 900 is satisfied with the reprogramming, the user 900 may communicate with the physician 906 to request approval for the programming, thereby making the programming the active programming for the user 900.

The physician 906 may evaluate the proposed reprogramming in view of the user's medical history and other factors and approve the reprogramming, deny the reprogramming, or approve the reprogramming with changes.

If the physician 906 approves with changes, then the flow moves back to the interaction between the user 900 and the sales representative 902, where the sales representative 902 may make changes to the programming (operation 908) and the user 900 may again evaluate the programming with the physician-provided changes. If the physician 906 denies the request for reprogramming, the user 900 may be informed of a reason via the user device.

If the physician 906 approves the reprogramming, then several operations occur. An invoice for an insurance company 912 may be automatically generated based on the approval (operation 914). The insurance company 912 may then perform conventional settlement operations to compensate the physician, request a copayment or coinsurance from the user 900, and provide the user 900 with an explanation of benefits statement. Additionally, the user's user device is provided a control message based on the physician's approval of the reprogramming. The control message may be used by the user device to allow the user 900 or the sales representative 902 to activate the programming, replacing the previous program.

It is understood that a program may include multiple programs and the IPG may be configured to operate with the identified program(s) for a time until the next re-optimization and reconfiguration. Ideally during this time, the patient has the best program available at that time. However, the patient may experience some neurological conditioning where the patient's neurological system becomes accustomed to the program in a way that the program loses some of its effect on the patient. The result may be the patient experiences more pain or different pain as the days or weeks go by. In an effort to avoid this neurological conditioning, the patient may be provided with a rotating or shifting program schedule. This altering program schedule may provide for neuroplasticity in the patient's neurological system; keeping the patient's neurological system confused and improving the performance or longevity of a program's efficacy. Such programming reduces the need to reprogram, thereby reducing power consumption in the devices in the neuromodulation system and increasing patient quality of life.

Thus, in an embodiment, two or more programs may be cycled on the IPG. The programs may be altered on a regular basis (e.g., changing every seven days) or on an irregular basis (e.g., changing randomly within a five to seven day range). When more than two programs are cycled, the order of the programs may be regular (e.g., cycling in sequence) or irregular (e.g., cycling arbitrarily).

In an example, a burst waveform may run for a specified period before the system automatically shifts to a high rate wave form, with cycling between programs. To avoid a period where pain relief and/or therapeutic effect from the first waveforms (A) ends before the therapeutic effect of the next waveform (B) begins, waveform B may be initiated prior to the termination of waveform A.

Figure 10:
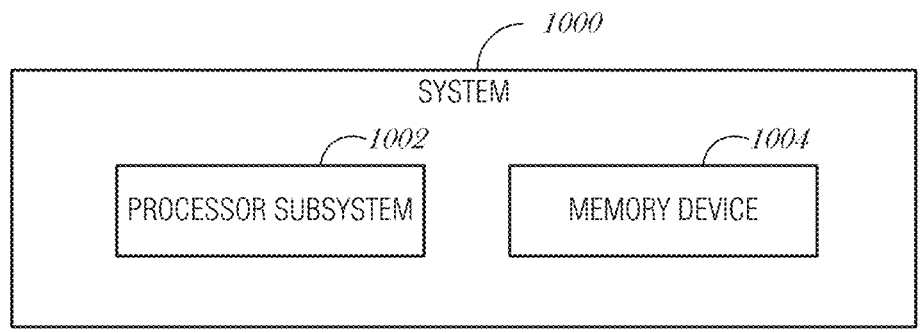
FIG. 10 illustrates, by way of example, an embodiment of a system that provides IPG control.

FIG. 10 illustrates, by way of example, an embodiment of a system 1000 that provides IPG control. The system 1000 may take on one of many forms. The system 1000 may be a remote control or other external device used by a patient or clinician, such as a user device 702.

The system 1000 includes a processor subsystem 1002 and a memory 1004. The processor subsystem 1002 may be any single processor or group of processors that act cooperatively. The memory 1004 may be any type of memory, including volatile or non-volatile memory. The memory 1004 may include instructions, which when executed by the processor subsystem 1002, cause the processor subsystem 1002 to receive at an application executing on a user device, a request to modify the application, transmit the request to an administrative user device for approval, receive a response to the request from the administrative user device, and modify a functionality of the application in response to receiving the response.

In an embodiment, the request to modify the application comprises a request to add a new feature to the application.

In an embodiment, the response is provided by a physician using the administrative user device.

In an embodiment, the instructions may include instructions to connect with an application repository to obtain a different version of the application after receiving the response to the request. In such an embodiment, modifying the functionality of the application comprises installing the different version of the application in place of the application. For example, the app developer may periodically or regularly release newer versions of the app. For the user to install the app, the user may need to have approval from their physician first. In such an embodiment, modifying the functionality of the application in response to receiving the response comprises enabling the new feature in the application. The new feature may be enabled by installing a plug-in, unlocking a previously locked feature, or downloading a new version of the app, for example.

In an embodiment, the request to modify the application comprises a request to modify stimulation parameters of an implantable pulse generator. In such an embodiment, modifying the functionality of the application in response to receiving the approval comprises updating the application to program the implantable pulse generator with stimulation parameters. The application may be configured to allow the user to test a new programming routine for testing, but to implement a new programming routine for semi-permanent use, the user may first need approval from their physician.

In an embodiment, the request to modify the application to modify stimulation parameters is made after an evaluation period. The evaluation period allows the user to test different stimulation parameters to determine which may work best for them at that point in time. Thus, the evaluation period includes an interaction with a technician to systematically test various stimulation parameters. The technician may the a physician, clinician, specialist, device manufacturer representative, etc.

In an embodiment, the response to the request is an approval with changes, and the memory 1004 includes instructions which when executed by the processor subsystem 1002, cause the processor subsystem to adjust stimulation parameters based on the approval with changes for additional evaluation.

In an embodiment, the memory 1004 includes instructions which when executed by the processor subsystem 1002, cause the processor subsystem 1002 to resubmit the request for approval after adjustments to the stimulation parameters.

In an embodiment, the response to the request is a denial of the request, and wherein the memory 1004 includes instructions which when executed by the processor subsystem 1002, cause the processor subsystem 1002 to present a notification on the user device, the notification including a reason why the request was denied.

In an embodiment, the user device comprises a smartphone.

Figure 11:
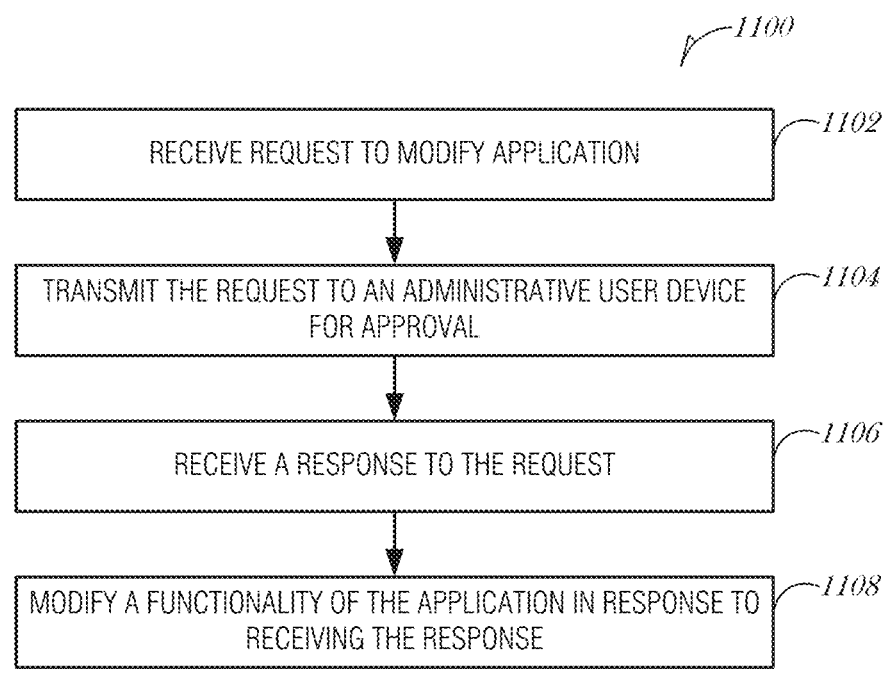
FIG. 11 illustrates, by way of example, an embodiment of a method for controlling an IPG.

FIG. 11 illustrates, by way of example, an embodiment of a method 1100 for controlling an IPG. At 1102, a request to modify an application is received at the application executing on a user device. In an embodiment, the request to modify the application comprises a request to add a new feature to the application.

At 1104, the request is transmitted to an administrative user device for approval.

At 1106, a response to the request is received from the administrative user device (e.g. user device 702). In an embodiment, the response is provided by a physician using the administrative user device.

At 1108, a functionality of the application is modified in response to receiving the response.

In an embodiment, the method 1100 includes connecting with an application repository to obtain a different version of the application after receiving the response to the request, and in such an embodiment, modifying the functionality of the application comprises installing the different version of the application in place of the application.

In an embodiment, modifying the functionality of the application in response to receiving the response comprises enabling the new feature in the application.

In an embodiment, the request to modify the application comprises a request to modify stimulation parameters of an implantable pulse generator. In a further embodiment, modifying the functionality of the application in response to receiving the approval comprises updating the application to program the implantable pulse generator with stimulation parameters.

In an embodiment, the request to modify the application to modify stimulation parameters is made after an evaluation period. In a further embodiment, the evaluation period includes an interaction with a technician to systematically test various stimulation parameters.

In an embodiment, the response to the request is an approval with changes, and in such an embodiment, the method 1100 includes adjusting stimulation parameters based on the approval with changes for additional evaluation. In a further embodiment, the method 1100 includes resubmitting the request for approval after adjustments to the stimulation parameters.

In an embodiment, the response to the request is a denial of the request, and in such an embodiment, the method 1100 includes presenting a notification on the user device, the notification including a reason why the request was denied.

Embodiments may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer) For example, a machine-readable storage device may include read-only memory (ROM), random-access memory (RAM), magnetic disk storage media, optical storage media, flash-memory devices, and other storage devices and media.

A processor subsystem may be used to execute the instruction on the machine-readable medium. The processor subsystem may include one or more processors, each with one or more cores. Additionally, the processor subsystem may be disposed on one or more physical devices. The processor subsystem may include one or more specialized processors, such as a graphics processing unit (GPU), a digital signal processor (DSP), a field programmable gate array (FPGA), or a fixed function processor.

Figure 12:
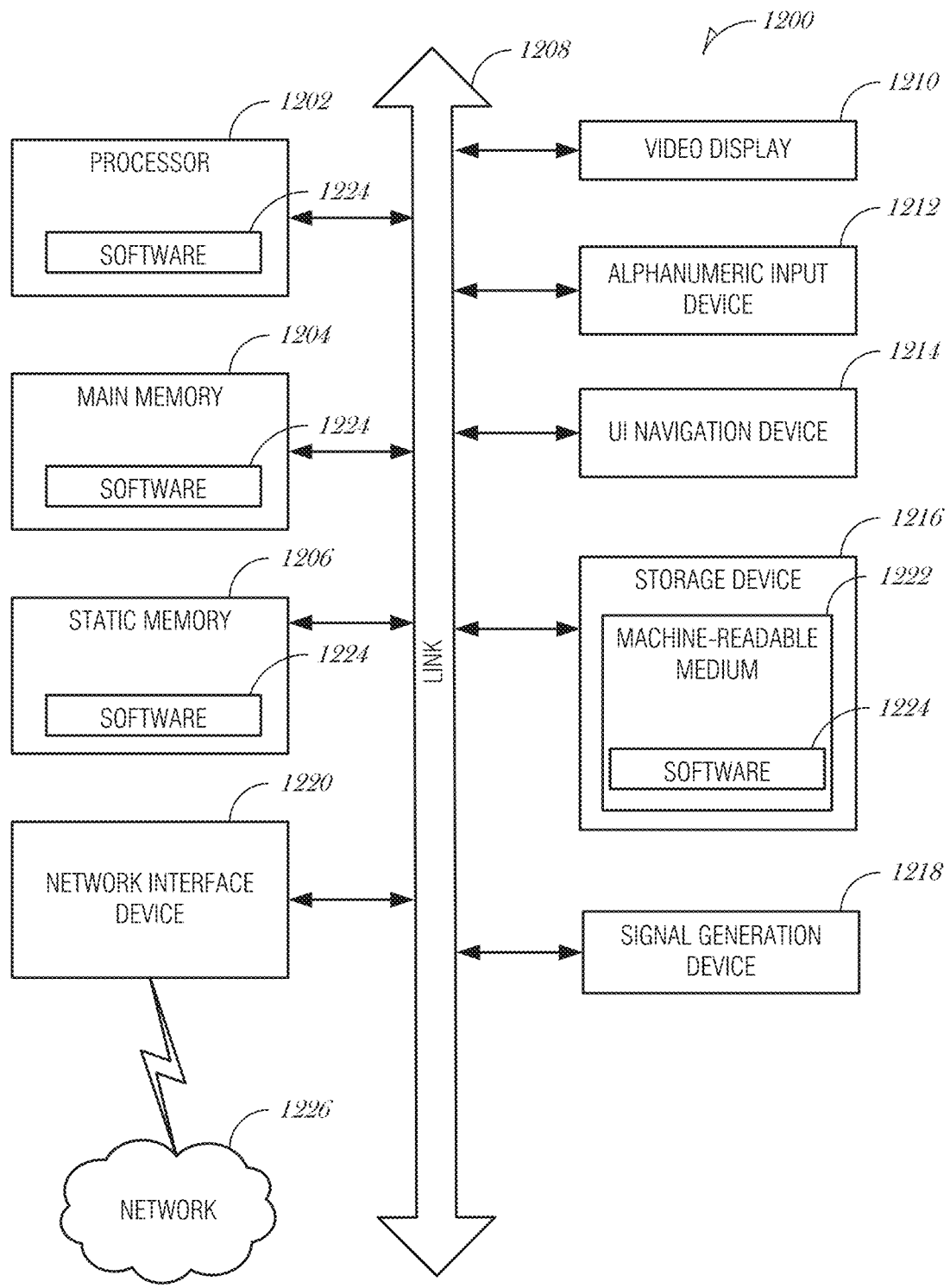
FIG. 12 is a block diagram illustrating a machine in the example form of a computer system, within which a set or sequence of instructions may be executed to cause the machine to perform any one of the methodologies discussed herein, according to an example embodiment.

FIG. 12 is a block diagram illustrating a machine in the example form of a computer system 1200, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may a personal computer (PC), a tablet PC, a hybrid tablet, a personal digital assistant (PDA), a mobile telephone, an implantable pulse generator (IPG), an external remote control (RC), a Clinician's Programmer (CP), an External Trial Stimulator (ETS), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1200 includes at least one processor 1202 (e.g., a central processing unit (CPU), a graphics processing unit (GPU) or both, processor cores, compute nodes, etc.), a main memory 1204 and a static memory 1206, which communicate with each other via a link 1208 (e.g., bus). The computer system 1200 may further include a video display unit 1210, an alphanumeric input device 1212 (e.g., a keyboard), and a user interface (UI) navigation device 1214 (e.g., a mouse). In one embodiment, the video display unit 1210, input device 1212 and UI navigation device 1214 are incorporated into a touch screen display. The computer system 1200 may additionally include a storage device 1216 (e.g., a drive unit), a signal generation device 1218 (e.g., a speaker), a network interface device 1220, and one or more sensors (not shown), such as a global positioning system (GPS) sensor, compass, accelerometer, or other sensor.

The storage device 1216 includes a machine-readable medium 1222 on which is stored one or more sets of data structures and instructions 1224 (e.g., software) embodying or utilized by any one or more of the methodologies or functions described herein. The instructions 1224 may also reside, completely or at least partially, within the main memory 1204, static memory 1206, and/or within the processor 1202 during execution thereof by the computer system 1200, with the main memory 1204, static memory 1206, and the processor 1202 also constituting machine-readable media.

While the machine-readable medium 1222 is illustrated in an example embodiment to be a single medium, the term "machine-readable medium" may include a single medium or multiple media (e.g., a centralized or distributed database, and/or associated caches and servers) that store the one or more instructions 1224. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1224 may further be transmitted or received over a communications network 1226 using a transmission medium via the network interface device 1220 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A system comprising:
    an implantable medical device including an implantable pulse generator configured for implantation in a patient;
    an administrative device configured for use by an administrator, wherein the administrator includes a physician, a clinician, a specialist, a sales representative, an insurance representative, or a customer support representative; and a user device configured for use by the patient to communicate with the administrative device and the implantable medical device, wherein the user device is configured to execute an application having functional features indicative of functional capabilities of the application that are available for the patient to use, and the user device includes:

a processor; and a memory comprising instructions, which when executed by the processor, cause the processor to:

receive at the application executing on the user device, a request to modify the application, wherein the request to modify the application comprises a request to change the functional features for the application, wherein the request to change the functional features for the application includes a request to add a new functional feature to the application;

transmit the request to the administrative device for approval;

receive a response to the request from the administrative device, wherein the response is provided by the administrator using the administrative device; and modify a functionality of the application, in response to receiving the response, by changing the functional features for the application to thereby change the functional capabilities of the application that are available for the patient to use, wherein changing the functional features includes adding the new functional feature, and wherein the application is configured with the new functional feature disabled, and the new functional feature is added by enabling the new functional feature in the application.

2. The system of claim 1, further comprising instructions which when executed by the processor, cause the processor to connect with an application repository to connect with an application repository to obtain a different version of the application after receiving the response to the request; and wherein the instructions to modify the functionality of the application comprise instructions to install the different version of the application in place of the application.

3. The system of claim 1, wherein the response to the request is an approval with changes, and wherein the memory includes instructions which when executed by the processor, cause the processor to modify the application based on the approval with changes.

4. The system of claim 3, further comprising instructions which when executed by the processor, cause the processor to resubmit the request for approval.

5. The system of claim 1, wherein the response to the request is a denial of the request, and wherein the memory includes instructions which when executed by the processor, cause the processor to present a notification on the user device, the notification including a reason why the request was denied.

6. The system of claim 1, wherein the application is configured with the at least one functional feature enabled, and the request to change the functional features for the application comprises a request to disable the at least one functional feature.

7. A method implemented using a system having an implantable medical device including an implantable pulse generator configured for implantation in a patient, an administrative device configured for use by an administrator wherein the administrator includes a physician, a clinician, a specialist, a sales representative, an insurance representative, or a customer support representative, and a user device configured for use by the patient to communicate with the administrative device and the implantable medical device, the user device being configured to execute an application having functional features indicative of functional capabilities of the application that are available for the patient to use, the method comprising:

receiving at an application executing on the user device, a request to modify the application, wherein the request to modify the application comprises a request to change the functional features for the application, wherein the request to change the functional features for the application includes a request to add a new functional feature to the application;

transmitting the request to the administrative device for approval;

receiving a response of the request from the administrative device, wherein the response is provided by the administrator using the administrative device; and modifying a functionality of the application, in response to receiving the response, by changing the functional features for the application to thereby change the functional capabilities of the application that are available for the patient to use, wherein changing the functional features includes adding the new functional feature, and wherein the application is configured with the new functional feature disabled, and the new functional feature is added by enabling the new functional feature in the application.

8. The method of claim 7, further comprising:

connecting with an application repository to obtain a different version of the application after receiving the response to the request; and wherein modifying the functionality of the application comprises:

installing the different version of the application in place of the application.

9. The method of claim 7, wherein the application is configured with the at least one functional feature enabled, the request to change the functional features for the application comprises a request to remove at least one functional feature to the application, and the modifying the functionality of the application includes disabling the at least one functional feature.

10. The method of claim 7, wherein the response provided by the administrator using the administrative device is indicative of physician approval, the method further comprising invoicing an insurance company for the change in the functional features.

11. The method of claim 7, further comprising receiving at least a partial payment from the patient for the change in the functional features.

12. A non-transitory machine-readable medium including instructions, which when executed by a machine, cause the machine to use a system to perform a method, wherein the system has an implantable medical device including an implantable pulse generator configured for implantation in a patient, an administrative device configured for use by an administrator wherein the administrator includes a physician, a clinician, a specialist, a sales representative, an insurance representative, or a customer support representative, and a user device configured for use by the patient to communicate with the administrative device and the implantable medical device and configured to execute an application having functional features indicative of functional capabilities of the application that are available for the patient to use, the method performed including:

receive at an application executing on the user device, a request to modify the application, wherein the request to modify the application comprises a request to change the functional features for the application, wherein the request to change the functional features for the application includes a request to add a new functional feature to the application;

transmit the request to the administrative device for approval;

receive a response of the request from the administrative device, wherein the response is provided by the administrator using the administrative device; and modify a functionality of the application, in response to receiving the response, by changing the functional features for the application to thereby change the functional capabilities of the application that are available for the patient to use, wherein changing the functional features includes adding the new functional feature, and wherein the application is configured with the new functional feature disabled, and the new functional feature is added by enabling the new functional feature in the application.

13. The non-transitory machine-readable medium of claim 12, further comprising:

connect with an application repository to obtain a different version of the application after receiving the response to the request; and wherein the modify the functionality of the application comprises install the different version of the application in place of the application.

14. The non-transitory machine-readable medium of claim 12, wherein the modify the functionality of the application in response to receiving the approval comprises update the application to program the implantable pulse generator with stimulation parameters.

* * * * *